United States Patent [19]

Akatsu et al.

[11] Patent Number: 5,191,140
[45] Date of Patent: Mar. 2, 1993

[54] PROCESS FOR PRODUCING OLEFIN OLIGOMER

[75] Inventors: Makoto Akatsu; Satoru Miyaji; Tatsuya Kawamura, all of Tokuyama, Japan

[73] Assignee: Idemitsu Petrochemical Co., Ltd., Tokyo, Japan

[21] Appl. No.: 756,508

[22] Filed: Sep. 9, 1991

[30] Foreign Application Priority Data

Sep. 20, 1990 [JP] Japan .................. 2-251446

[51] Int. Cl.$^5$ .............................. C07C 2/02
[52] U.S. Cl. .................. 585/525; 502/150; 502/172
[58] Field of Search .......................... 585/525

[56] References Cited

U.S. PATENT DOCUMENTS

| | | | |
|---|---|---|---|
| 3,382,291 | 5/1968 | Brennan | 260/683.15 |
| 3,763,244 | 10/1973 | Shubkin | 260/676 R |
| 3,997,621 | 12/1976 | Brennan | 260/683.95 |
| 4,409,415 | 10/1983 | Morganson et al. | 585/525 |
| 4,436,947 | 3/1984 | Morganson et al. | 585/525 |
| 4,849,572 | 7/1989 | Chen et al. | 585/525 |

FOREIGN PATENT DOCUMENTS 49-11804 12/1972 Japan .

Primary Examiner—Patrick P. Garvin
Assistant Examiner—Brent M. Preebles
Attorney, Agent, or Firm—Frishauf, Holtz, Goodman & Woodward

[57] ABSTRACT

A process for producing an olefin oligomer by the polymerization of an olefin in the presence of boron trifluoride as a catalyst, and further in the co-presence of water and/or an alcohol and a carboxylic acid anhydride as a co-catalyst. The process has advantages that (i) olefin oligomers having a low viscosity can be produced at high yields, (ii) the production efficiency can be improved by decreasing the time required for the reaction, (iii) the amount of the co-catalyst required can be decreased, and (iv) the viscosity of an olefin oligomer to be obtained can be freely controlled by changing the amounts of the olefin, the catalyst, the co-catalyst, etc.

17 Claims, No Drawings

PROCESS FOR PRODUCING OLEFIN OLIGOMER

FIELD OF THE INVENTION

The present invention relates to a process for producing an olefin oligomer, more specifically to a process for producing a low-viscosity olefin oligomer useful as a base fluid for a lubricant, etc., at high yields.

DESCRIPTION OF THE PRIOR ARTS

Olefin oligomers obtained by the polymerization of olefins, particularly α-olefins having 6 to 18 carbon atoms, or olefin oligomers containing a large content of oligomers of not smaller than trimers in particular, are useful as a base fluid for lubricants. In the fields of use of lubricants in an automobile engine oil, etc., it is required not only to decrease the fuel consumption but also to improve the low-temperature fluidity. Therefore, attempts have been made to decrease lubricant viscosity. For this reason, for a base fluid for lubricants, it is also preferred to use an olefin oligomer having a viscosity, measured at 100° C., of smaller than 4 centistokes (to be abbreviated as "cSt" hereinafter).

As a process for producing an olefin oligomer, there is known a process in which an olefin is subjected to cationic polymerization in the presence, as a catalyst, of a Lewis acid such as aluminum chloride, boron trifluoride, or the like.

In fact, however, nothing but olefin oligomers having a high viscosity can be obtained by the process using aluminum chloride as a catalyst.

On the other hand, in the process using boron trifluoride as a catalyst, boron trifluoride has no activity as an olefin polymerizing catalyst when used alone, and it is general practice to use a co-catalyst in combination with boron trifluoride when an olefin is polymerized; and, an alcohol, water and a carboxylic acid are separately used as a co-catalyst (U.S. Pat. No. 3,382,291, U.S. Pat. No. 3,763,244, and Japanese Unexamined Patent Publication No. Sho 49-11804).

The above processes have an advantage that an olefin oligomer having a relatively low viscosity can be obtained. However, the process using an alcohol or water as a co-catalyst has a defect in that when an attempt is made to obtain an olefin oligomer having a low viscosity of smaller than 4 cSt at 100° C., the yield of the olefin oligomer is very low. In the process using a carboxylic acid as a co-catalyst, the yield is improved to some extent as compared with the above processes, and yet it is still low. Further, this process involves disadvantages that a large amount of the co-catalyst is required, the polymerization temperature is required to be as low as possible, and the like. Thus, this process cannot be said to be efficient.

Further, as another process, an attempt was made to use boron trifluoride as a catalyst, an aliphatic alcohol and a polyol such as ethylene glycol, etc., as a co-catalyst and optionally an aliphatic ketone (U.S. Pat. No. 4,409,415 and U.S. Pat. No. 4,436,947), or another attempt was also made to carry out a process in which boron trifluoride is used as a catalyst, water or alcohol is used as a co-catalyst and an ester is added as a catalyst modifier (U.S. Pat. No. 3,997,621). The former process aims to improve the recovery ratio of an oligomer having a viscosity of 4 cSt at 100° C. when oligomers having viscosities of 4 cSt and 6 cSt at 100° C. are co-produced by distillation and separation of a polymerization product. Thus, this process is not intended to directly produce an oligomer having a viscosity of 4 cSt by polymerization. The ester used as a catalyst modifier in the latter process is used as a co-catalyst (U.S. Pat. No. 3,382,291), and the catalyst modifier is hence considered to be one of co-catalysts. Therefore, the latter process is substantially equivalent to a process in which a plurality of components are used as a co-catalyst. This process makes it possible to directly produce an oligomer having a viscosity of 4 cSt at relatively high yields. However, this process has never been efficient since it involves disadvantages that a large amount of the catalyst modifier is required and the production takes long since the polymerization rate is low.

SUMMARY OF THE INVENTION

It is an object of the present invention to provide a process for producing an olefin oligomer, which overcomes the above problems and has advantages that (i) an olefin oligomer having a low viscosity can be produced at high yields, (ii) the production efficiency can be improved by decreasing the time required for the reaction, (iii) the amount of the co-catalyst required can be decreased, and (iv) the viscosity of an olefin oligomer to be obtained can be freely controlled by changing the amounts of the olefin, the catalyst, the co-catalyst, etc., and other advantages.

The present inventors have made studies of co-catalysts used in combination with a boron trifluoride catalyst in order to achieve the above object, and as a result, found that the above object can be achieved by using water and/or an alcohol and a carboxylic acid anhydride in combination with boron trifluoride. On the basis of the this finding, the present invention has been completed.

That is, the gist of the present invention exists in a process for producing an olefin oligomer which comprises polymerizing an olefin in the presence of boron trifluoride as a catalyst, and further in the co-presence of water and/or an alcohol and a carboxylic acid anhydride as a co-catalyst.

DETAILED DESCRIPTION OF THE INVENTION

The present invention will be detailed hereinafter.

The olefin used as a starting material in the process for producing an olefin oligomer, provided by the present invention, is not specially limited, and α-olefins, internal olefins and a mixture of these may be used if these olefins have at least two carbon atoms. Preferred is an α-olefin having 6 to 18 carbon atoms, and more preferred is an α-olefin having 8 to 14 carbon atoms.

The process for producing an olefin oligomer, provided by the present invention, has its characteristic feature in that water and/or an alcohol and a carboxylic acid anhydride are co-used as a co-catalyst for the polymerization of the above olefin in the presence of boron trifluoride as a catalyst. When water and/or an alcohol and a carboxylic acid anhydride are used in combination as a co-catalyst, a synergistic effect is produced, and due to the synergistic effect, remarkable effects are produced on improvement in the yields of a low-viscosity oligomer, improvement in production efficiency by decreasing the reaction time, a decrease in the amount of the catalyst required, and the like as compared with the use, as a co-catalyst, of water, an alcohol or a carboxylic acid anhydride alone.

The components of the co-catalyst used in the present invention are combined as follows.
(a) Water-carboxylic acid anhydride
(b) Alcohol-carboxylic acid anhydride
(c) Water-alcohol-carboxylic acid anhydride Although not specially limited, the alcohol as one component of the co-catalyst is selected from primary alcohols and/or secondary alcohols. Examples of the primary alcohols are those having 1 to 10 carbon numbers, such as methyl alcohol, ethyl alcohol, n-propyl alcohol, n-butyl alcohol, n-octyl alcohol, etc. Examples of the secondary alcohols are those having 3 to 10 carbon atoms, such as iso-propyl alcohol, sec-butyl alcohol, etc. Mixtures of these alcohols may be used. It is, however, preferred to avoid the use of a tertiary alcohol, since tertiary alcohols are unstable in the presence of boron trifluoride and easily dehydrated.

Although not specially limited, the carboxylic acid anhydride as one component of the co-catalyst is selected from aliphatic carboxylic acid anhydrides such as acetic anhydride, propionic anhydride, butyric anhydride, valeric anhydride, succinic anhydride, and/or aromatic carboxylic acid anhydrides such as benzoic anhydride, phthalic anhydride, etc. It is, however, preferred to avoid the use of formic anhydride, since it is unstable and liable to be decomposed at room temperature.

The amount ratio between the boron trifluoride as a catalyst and the "water and/or an alcohol and a carboxylic acid anhydride" is not specially limited. In general, however, the (boron trifluoride)/(water and/or the alcohol and the carboxylic acid anhydride) molar ratio is 1.01 to 5.0, preferably 1.02 to 1.50. In this case, although not specially limited, the (carboxylic acid anhydride)/(water and/or the alcohol) molar ratio is generally 0.1 to 2.0, preferably 0.2 to 1.0.

Further, although not specially limited, the amount of water and/or the alcohol as a co-catalyst per mole of an olefin is generally 0.1 to 10 mol %, preferably 0.2 to 5 mol %.

The water, alcohol and carboxylic acid anhydride as a co-catalyst are wholly or partially present in the reaction system as a complex with boron trifluoride.

In the present invention, the polymerization of the olefin in the presence of a boron trifluoride complex may be carried out by a process in which boron trifluoride as a catalyst and water and/or an alcohol and a carboxylic acid anhydride as a co-catalyst are respectively introduced into the reaction system to form the boron trifluoride complex. Or, alternatively, the above polymerization may be carried out by a process in which a boron trifluoride complex is separately prepared, and this boron trifluoride complex and boron trifluoride are together introduced into the reaction system. In addition, the boron trifluoride complex can be easily prepared by blowing boron trifluoride gas into water, an alcohol or a carboxylic acid anhydride.

The amount of heat generated when the complex is formed is large. In view of the ease in controlling the reaction, it is therefore preferred to employ the process in which the boron trifluoride complex is separately prepared and then introduced into the reaction system.

No solvent is particularly required for the polymerization of the olefin. However, a solvent may be used as required. Such a solvent is selected from halogenated hydrocarbon such as carbon tetrachloride, chloroform, methylene chloride, etc., linear saturated hydrocarbons such as pentane, hexane, heptane, etc., and alicyclic hydrocarbons such as cyclohexane, methylcyclohexane, etc.

Although not specially limited, the polymerization conditions are as follows. The polymerization temperature is generally $-10°$ to $80°$ C., preferably $0°$ to $40°$ C. The pressure for charging boron trifluoride is generally 0 to 35 kg/cm$^2$G, preferably 0.05 to 5 kg/cm$^2$G.

The polymerization time is generally 0.25 to 8 hours, preferably 0.5 to 4 hours.

After the polymerization, the catalyst is removed from the polymerization product, and an olefin oligomer is recovered.

For the removal of the catalyst, there are two methods. One is a method wherein a catalyst is deactivated simply with water or an alkali aqueous solution, followed by washing to remove the catalyst, and the other is a method wherein a catalyst is removed from a polymerization product. In the latter method, at first, the boron trifluoride complex is separated from the polymerization product. As means for this separation, preferred is means of precipitation separation or centrifugal separation. Thereafter, boron trifluoride is removed from the polymerization product from which the boron trifluoride complex has been removed. There are a variety of methods for this removal. Preferred are a method in which the pressure in the reaction system containing the polymerization product is reduced below atmospheric pressure, a method in which an inert gas such as nitrogen, argon, helium, or the like is blown into the polymerization product, and a method in which the polymerization product is heated approximately to a temperature of 80° C. or lower.

The catalyst is preferably removed from the polymerization product by a method in which the catalyst complex is first separated and boron trifluoride is then removed as described above. However, there may be employed a method in which the boron trifluoride is first removed from the polymerization product and the boron trifluoride complex is then separated.

The boron trifluoride which has been removed above can be directly recycled as a catalyst for the polymerization of an olefin. Further, the boron trifluoride complex which has been separated above can be also directly recycled as a catalyst for the polymerization of an olefin without any decrease in the activity. Moreover, it may be mixed with the co-catalyst before use.

It is the general practice to hydrogenate the above-obtained polymerization product in order to obtain a final product. In general, after an unreacted monomer and a dimer are separated from the polymerization product, the polymerization product is subjected to hydrogenation treatment. The separated unreacted monomer and dimer can be properly recycled to the reaction system. In the alternative method, the unreacted monomer alone is separated from the polymerization product by distillation, and the hydrogenation treatment is carried out. Further, the hydrogenation treatment may be carried out before the distillation of the polymerization product.

EXAMPLES

The present invention will be further explained hereinbelow by reference to Examples.

EXAMPLE 1 n-Butanol and acetic anhydride were used as a co-catalyst for the polymerization of 1-decene, and the n-butanol was added as a complex with boron trifluoride. The details are as follows.

A polymerization flask having a stirrer, a condenser, a thermometer and a gas introducing tube was subjected to substitution of dry nitrogen gas, and charged with 100 ml of 1-decene, 1.68 mol, per 100 mol of the 1-decene, of a boron trifluoride-n-butanol complex (molar ratio 1:1) and 0.42 mol, per 100 mol of the 1-decene, of acetic anhydride. The mixture was cooled to 20° C., and boron trifluoride gas was blown into the mixture to start the polymerization. The polymerization was continued for 2 hours with cooling the mixture to keep its temperature at 20° C. After the polymerization, 100 ml of 5% ammonia water was added to deactivate the catalyst. And, the polymerization product was washed with water and dried, and an unreacted olefin and low-molecular-weight oligomers having 20 or less carbon atoms were distilled off to give an olefin oligomer. Table 1 shows the polymerization conditions, the conversion of the olefin and the yield and properties of the olefin oligomer. The "oligomer composition" in Table 1 shows the result of analysis of the polymerization product which had just been washed with water and dried.

EXAMPLES 2 AND 3

The procedures of Example 1 were repeated except that the amounts of the co-catalysts and the polymerization temperature were changed. Table 1 shows the polymerization conditions, the conversion of the olefin and the yield and properties of the olefin oligomer in each Example.

EXAMPLE 4

The procedures of Example 1 were repeated except that the n-butanol as a co-catalyst was replaced with water and that the polymerization conditions were changed. Table 1 shows the polymerization conditions, the conversion of the olefin and the yield and properties of the olefin oligomer.

COMPARATIVE EXAMPLES 1 AND 2

The procedures of Example 1 were repeated except that the acetic anhydride as a co-catalyst was not used and that the polymerization conditions were changed. Table 1 shows the polymerization conditions, the conversion of the olefin and the yield and properties of the olefin oligomer.

COMPARATIVE EXAMPLES 3-6

The procedures of Example 1 were repeated except that the two co-catalysts were replaced with water (Comparative Example 3), acetic anhydride (Comparative Example 4), acetic acid (Comparative Example 5) or n-valeric acid (Comparative Example 6) alone and that the polymerization conditions were changed. Table 1 shows the polymerization conditions, the conversion of the olefin and the yield and properties of the olefin oligomer in each Comparative Example.

COMPARATIVE EXAMPLE 7-9

The procedures of Example 1 were repeated except that the acetic anhydride as a co-catalyst was replaced with n-butyl acetate (Comparative Examples 7 and 8) or methyl butyrate (Comparative Example 9) and that the polymerization conditions were changed. Table 1 shows the polymerization conditions, the conversion of the olefin and the yield and properties of the olefin oligomer in each Comparative Example.

COMPARATIVE EXAMPLE 10

The procedures of Example 1 were repeated except that the two co-catalysts were repalced with water and methyl butyrate and that the polymerization conditions were changed. Table 1 shows the polymerization conditions, the conversion of the olefin and the yield and properties of the olefin oligomer.

EXAMPLE 5

The procedures of Example 1 were repeated except that the olefin was changed to 1-octene. Table 2 shows the polymerization conditions, the conversion of the olefin and the yield and properties of the olefin oligomer.

COMPARATIVE EXAMPLES 11 AND 12

The procedures of Comparative Examples 2 and 7 were repeated except that the olefin was changed to 1-octene. Table 2 shows the polymerization conditions, the conversion of the olefin and the yield and properties of the olefin oligomer in each Comparative Example.

EXAMPLE 6

The procedures of Example 1 were repeated except that the olefin was changed to 1-dodecene. Table 3 shows the polymerization conditions, the conversion of the olefin and the yield and properties of the olefin oligomer.

In Table 1, the results of Examples 1 to 4 in which water and/or an alcohol and a carboxylic acid anhydride were used as a co-catalyst clearly show that (i) olefin oligomers having a low viscosity can be obtained, that (ii) the reaction time can be decreased, and that (iii) the amount of the co-catalysts for use can be decreased, as compared with those of Comparative Examples 1 and 2 in which an alcohol alone was used, Comparative Example 3 in which water alone was used, Comparative Example 4 in which a carboxylic acid anhydride alone was used, Comparative Examples 5 and 6 in which a carboxylic acid alone was used, Comparative Examples 7 to 9 in which an alcohol and an ester were used and Comparative Example 10 in which water and an ester were used. Further, the results of Examples 1 to 4 in which the amounts and mixing ratio of the co-catalysts were changed show that the viscosity of the oligomer to be obtained can be controlled by changing these parameters.

In contrast, in Comparative Example 1 in which an alcohol alone was used, the yield of the oligomer was low and the viscosity of the oligomer was high. In Comparative Example 2 in which an alcohol alone was used, the reaction time was increased to increase the yield of the oligomer. In this case, however, the resultant oligomer showed a higher viscosity.

In any of Comparative Example 3 in which water alone was used, Comparative Example 4 in which a carboxylic acid anhydride alone was used and Comparative Examples 5 to 6 in which a carboxylic acid alone was used, the yield was low. Further, in Comparative Examples 7 to 9 in which an alcohol and an ester were used, the intended result was obtained if the reaction time was increased to as long as 8 hours (Comparative Example 7). However, when the reaction was set at 2 hours in the same manner as in Examples 1 to 4, the yields of the oligomers were low (Comparative Examples 8 and 9). In Comparative Example 10 in which water and an ester were used, the viscosity of the oligomer was high, or no oligomer having a low viscosity could be obtained.

The results in Tables 2 and 3 show that the use of 1-octene and 1-dodecene as an olefin also gave excellent results similarly to those of Examples in which 1-decene was used, shown in Table 1.

TABLE 1

|  | Ex. 1 | Ex. 2 | Ex. 3 | Ex. 4 | CEx. 1 | CEx. 2 | CEx. 3 |
|---|---|---|---|---|---|---|---|
| Olefin | 1-decene | 1-decene | 1-decene | 1-decene | 1-decene | 1-decene | 1-decene |
| (ml) | (100) | (100) | (100) | (100) | (100) | (100) | (100) |
| Co-catalyst |  |  |  |  |  |  |  |
| Water and/or alcohol(1) (mol) | n-butanol(4) (1.68) | n-butanol(4) (1.68) | n-butanol(4) (3.36) | water (1.68) | n-butanol(4) (0.84) | n-butanol(4) (0.38) | water(4) (4.31) |
| Carboxylic acid anhydride(1) (mol) | acetic anhydride (0.42) | acetic anhydride (0.84) | acetic anhydride (1.68) | acetic anhydride (1.68) | — | — | — |
| Others(1) (mol) | — | — | — | — | — | — | — |
| Temperature (°C.) | 20 | 20 | 10 | 20 | 60 | 60 | 15 |
| Time (hr) | 2 | 2 | 2 | 2 | 0.67 | 2 | 2 |
| Olefin conversion (%) | 96.0 | 84.4 | 97.0 | 76.8 | 78.1 | 87.6 | 24.7 |
| Oligomer composition(2) (%) |  |  |  |  |  |  |  |
| $C_{20}$ | 12.5 | 26.6 | 24.8 | 42.4 | 40.3 | 43.8 | 32.3 |
| $C_{30}$ | 70.5 | 67.1 | 67.8 | 55.0 | 53.9 | 43.9 | 57.8 |
| $C_{40+}$ | 17.0 | 6.3 | 7.8 | 2.6 | 5.8 | 12.3 | 9.9 |
| Yield of oligomer(3) (%) | 84.0 | 61.9 | 72.9 | 44.2 | 46.6 | 49.2 | 16.7 |
| Viscosity at 100° C. (cSt) | 3.84 | 3.61 | 3.68 | 3.58 | 3.93 | 4.09 | 3.83 |
| Viscosity index | 131 | 127 | 124 | 125 | 131 | 125 | 138 |

|  | CEx. 4 | CEx. 5 | CEx. 6 | CEx. 7 | CEx. 8 | CEx. 9 | CEx. 10 |
|---|---|---|---|---|---|---|---|
| Olefin | 1-decene | 1-decene | 1-decene | 1-decene | 1-decene | 1-decene | 1-decene |
| (ml) | (100) | (100) | (100) | (100) | (100) | (100) | (100) |
| Co-catalyst |  |  |  |  |  |  |  |
| Water and/or alcohol(1) (mol) | — | — | — | n-butanol(4) (1.68) | n-butanol(4) (1.68) | n-butanol(4) (5.04) | water (0.80) |
| Carboxylic acid anhydride(1) (mol) | acetic anhydride (0.42) | — | — | — | — | — | — |
| Others(1) (mol) | — | acetic acid(4) (6.78) | n-valeric acid(4) (3.36) | n-butyl acetate (1.68) | n-butyl acetate (1.68) | methyl acetate (5.04) | methyl acetate (0.80) |
| Temperature (°C.) | 20 | 10 | 20 | 20 | 20 | 10 | 15 |
| Time (hr) | 2 | 2 | 2 | 8 | 2 | 2 | 4.5 |
| Olefin conversion (%) | 13.0 | 95.0 | 77.1 | 99.4 | 50.4 | 67.9 | 99.8 |
| Oligomer composition(2) (%) |  |  |  |  |  |  |  |
| $C_{20}$ | — | 33.4 | 48.0 | 14.2 | 18.5 | 15.0 | 18.3 |
| $C_{30}$ | — | 57.1 | 48.6 | 70.4 | 74.0 | 74.6 | 66.7 |
| $C_{40+}$ | — | 9.5 | 3.4 | 15.4 | 7.5 | 10.4 | 15.0 |
| Yield of oligomer(3) (%) | 8.5 | 63.3 | 40.1 | 85.3 | 41.1 | 57.7 | 81.5 |
| Viscosity at 100° C. (cSt) | 3.88 | 3.71 | 3.67 | 3.83 | — | 3.65 | 4.00 |
| Viscosity index | 127 | 123 | 128 | 125 | — | 126 | 127 |

Notes: Ex. = Example, CEx = Comparative Example
(1) Amount (mol) of co-catalyst per 100 mol of olefin
(2) Results of analysis of polymerization product just after it was washed with water and dried.
(3) Yield of oligomers which were not smaller than trimers.
(4) Added as $BF_3$ complex.

TABLE 2

|  | Ex. 5 | CEx. 11 | CEx. 12 |
|---|---|---|---|
| Olefin | 1-octene | 1-octene | 1-octene |
| (ml) | (100) | (100) | (100) |
| Co-catalyst |  |  |  |
| Water and/or alcohol(1) (mol) | n-butanol(3) (1.68) | n-butanol(3) (0.38) | n-butanol(3) (1.68) |
| Carboxylic acid anhydride(1) (mol) | acetic anhydride (0.42) | — | — |
| Others(1) (mol) | — | — | n-butyl acetate (1.68) |
| Temperature (°C.) | 20 | 60 | 20 |
| Time (hr) | 2 | 2 | 8 |
| Yield of oligomer(2) (%) | 85.5 | 47.2 | 84.2 |
| Viscosity at 100° C. (cSt) | 2.51 | 2.92 | 2.49 |
| Viscosity index | 95 | 96 | 92 |

Notes: Ex. = Example, CEx = Comparative Example
(1) Amount (mol) of co-catalyst per 100 mol of olefin
(2) Yield of oligomers which were not smaller than trimers.
(3) Added as $BF_3$ complex.

TABLE 3

|  | Ex. 6 |
|---|---|
| Olefin | 1-dodecene |
| (ml) | (100) |

TABLE 3-continued

|  | Ex. 6 |
|---|---|
| Co-catalyst | |
| Water and/or alcohol(1) (mol) | n-butanol(3) (1.68) |
| Carboxylic acid anhydride(1) (mol) | acetic anhydride (0.42) |
| Others(1) (mol) | — |
| Temperature (°C.) | 20 |
| Time (hr) | 2 |
| Yield of oligomer(2) (%) | 83.8 |
| Viscosity at 100° C. (cSt) | 5.38 |
| Viscosity index | 145 |

Notes: Ex. = Example
(1) Amount (mol) of co-catalyst per 100 mol of olefin
(2) Yield of oligomers which were not smaller than trimers.
(3) Added as $BF_3$ complex.

According to the present invention, there is provided a process for producing olefin oligomers in which low-viscosity olefin oligomers can be produced at high yields, the production efficiency can be improved due to a decrease in the reaction time, the amount of the co-catalyst for use can be decreased, and the viscosity of the olefin oligomers to be obtained can be controlled.

Therefore, there can be provided olefin oligomers which are excellent as a base fluid for an automobile engine oil which is required to have improved low-temperature fluidity.

Further, the olefin oligomers provided by the present invention are excellent as a material for lubricant base fluid for a gas turbine engine oil, aircraft hydraulic oil, insulating oil, etc., in addition to the above. These olefin oligomers can be converted to excellent lubricant base fluid by hydrogenating them.

Therefore, the present invention will make a great contribution to the field of lubricant manufacturing industry and the use of lubricants.

What is claimed is:

1. A process for producing an olefin oligomer, which comprises polymerizing an α-olefin having 6 to 16 carbon atoms in the presence of boron trifluoride as a catalyst and further in the co-presence of a co-catalyst selected from the group consisting of at least two of water, an alcohol and a carboxylic acid anhydride.

2. The process according to claim 1, wherein the alcohol is present and is a primary alcohol and/or a secondary alcohol.

3. The process according to claim 2, wherein the alcohol is a primary alcohol having 1 to 10 carbon atoms.

4. The process according to claim 2, wherein the alcohol is a secondary alcohol having 3 to 10 carbon atoms.

5. The process according to claim 1, wherein the carboxylic acid anhydride is present and is an aliphatic carboxylic acid anhydride and/or an aromatic carboxylic acid anhydride.

6. The process according to claim 5, wherein the carboxylic acid anhydride is present and is at least one aliphatic carboxylic acid anhydride selected from the group consisting of acetic anhydride, propionic anhydride, butyric anhydride, valeric anhydride and succinic anhydride.

7. The process according to claim 5, wherein the aromatic carboxylic acid anhydride is at least one member selected from the group consisting of benzoic anhydride and phthalic anhydride.

8. The process according to claim 1, wherein the catalyst and the co-catalyst are present in a (boron trifluoride)/(water and/or an alcohol and a carboxylic acid anhydride) molar ratio of 1.01 to 5.0.

9. The process according to claim 1, wherein the co-catalyst is present in a carboxylic acid anhydride/(water and/or an alcohol) molar ratio of 0.1 to 2.0.

10. The process according to claim 1, wherein the water, the alcohol and the carboxylic acid anhydride are wholly or partly present as a complex with the boron trifluoride.

11. The process according to claim 1, which further comprises the reaction being carried out in a solvent.

12. The process according to claim 11, wherein the solvent is at least one member selected from the group consisting of hydrogenated hydrocarbons, linear saturated hydrocarbons and alicyclic hydrocarbons.

13. The process according to claim 1, wherein the reaction is carried out at a temperature between −10° C. and 80° C. under a pressure of 0 to 35 kg/cm²G for charging the boron trifluoride.

14. The process according to claim 1, wherein the alcohol is present and is selected from the group consisting of methyl alcohol, ethyl alcohol, n-propyl alcohol, n-butyl alcohol, n-octyl alcohol, iso-propyl alcohol, sec-butyl alcohol and mixtures thereof.

15. The process according to claim 14, wherein the carboxylic acid anhydride is present and is selected from the group consisting of acetic anhydride, propionic anhydride, butyric anhydride, valeric anhydride, succinic anhydride, benzoic anhydride, phthalic anhydride and mixtures thereof.

16. The process according to claim 15, wherein the boron trifluoride, the water, the alcohol and the carboxylic acid anhydride are present in amounts such that $$(a) \frac{\text{boron trifluoride}}{\text{water + alcohol + carboxylic acid anhydride}}$$

is in a molar ratio of 1.02 to 1.50 and $$(b) \frac{\text{carboxylic acid anhydride}}{\text{water + alcohol}}$$

is in a molar ratio of 0.2 to 1.0 and (c) the amount of water and alcohol per mole of the olefin is 0.2 to 5 mole %.

17. The process according to claim 16, wherein the polymerizing is carried out at a temperature of 0° to 40° C., at a pressure of 0 to 5 kg/cm²G and for a period of time of 0.5 to 4 hours.

* * * * *